(12) United States Patent
Kanda et al.

(10) Patent No.: US 6,360,589 B1
(45) Date of Patent: *Mar. 26, 2002

(54) LIQUID CHROMATOGRAPHY AND COLUMN PACKING MATERIAL

(75) Inventors: Taketoshi Kanda; Aya Ohkubo; Yutaka Ohtsu; Michihiro Yamaguchi, all of Yokohama (JP)

(73) Assignee: Shiseido Company, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,880

(22) PCT Filed: Mar. 27, 1998

(86) PCT No.: PCT/JP98/01372

§ 371 Date: Nov. 25, 1998

§ 102(e) Date: Nov. 25, 1998

(87) PCT Pub. No.: WO98/44344

PCT Pub. Date: Oct. 8, 1998

(30) Foreign Application Priority Data

Mar. 28, 1997 (JP) .............................................. 9-078159

(51) Int. Cl.[7] .......................... G01N 30/00; B01D 15/08; B32B 3/26
(52) U.S. Cl. ................. 73/61.52; 210/198.2; 428/304.4
(58) Field of Search ........................... 73/61.52, 61.53, 73/61.55, 61.56, 61.59; 210/198.2; 428/304.4, 403, 405

(56) References Cited

U.S. PATENT DOCUMENTS

| 4,743,377 A | * | 5/1988 | Ohtsu et al. ................. 210/635 |
| 4,801,445 A | * | 1/1989 | Fukui et al. ................... 424/69 |
| 4,818,614 A | * | 4/1989 | Fukui et al. ................. 428/403 |
| 4,882,225 A | * | 11/1989 | Fukui et al. ................. 428/405 |
| 5,135,649 A | * | 8/1992 | Kanda et al. ............. 210/198.2 |
| 5,145,578 A | * | 9/1992 | Tokubo et al. ........... 210/198.2 |
| 5,672,422 A | * | 9/1997 | Kanda et al. ............. 428/304.4 |
| 5,738,783 A | * | 4/1998 | Shirota et al. ........... 210/198.2 |

FOREIGN PATENT DOCUMENTS

| JP | 61-65159 | | 4/1986 | |
| JP | 5-72190 | | 3/1993 | |
| JP | 8050120 | * | 2/1996 | .......... G01N/30/08 |
| JP | 8262004 | | 10/1996 | |

OTHER PUBLICATIONS

J. Calvin, Eli, Grushka, Jack Cazes, Pylilis R. Broww, "Advances in Chromatography," vol. 17, Marcel Dekker, Inc., New York and Basel, 1979.

* cited by examiner

Primary Examiner—Thomas P. Noland
Assistant Examiner—Jay L. Politzer
(74) Attorney, Agent, or Firm—Ladas & Parry (57) ABSTRACT

A liquid chromatograph and a column packing material effectively condensing cationic specimen and exhibiting a high resolution. The liquid chromatograph includes a pre-focusing column (30, 40) having a volume of less than 2.0 milliliters and packed with a column packing material, in which a porous support is coated by a silicone polymer having a Si—R—X (R is a spacer part, X is a sulfonic group) bond and a Si—R' (R' is a hydrophilic group) bond, wherein the specimen to be analyzed is supplied to the pre-focusing column in the state dispersed in a solvent for condensation. The condensed specimen is then separated in a separation column (16, 43) used for separating the specimen dispersed in the solvent, and the separated specimen is analyzed by a detector (17, 41).

15 Claims, 8 Drawing Sheets

LIQUID CHROMATOGRAPHY AND COLUMN PACKING MATERIAL

TECHNICAL FIELD

The present invention relates to liquid chromatograph, and more particularly to a liquid chromatograph having a pre-focusing column used for condensing a specimen to be analyzed, and a method of analysis of a specimen including a condensation process.

PRIOR ART

Liquid chromatography is used extensively in the field of chemical analysis for separating and analyzing specimen quantitatively. Particularly, the liquid chromatography, which uses a semi-micro column having an inner diameter of 1–2 mm, is advantageous for providing a high sensitivity, high resolution and high precision analysis. Thus, intensive investigations are being made on the art of liquid chromatography.

In particular, there is an emphasis in the art of using a semi-micro column or a short general-purpose column (such as the one having an inner diameter of 4 mm and a length of 10 mm or 20 mm) for a pre-focusing column, not for a separation column, wherein the pre-focusing column is used for condensing the specimen.

The pre-focusing column is provided separately to the usual separation column in a liquid chromatograph, and is used prior to the separation of the specimen in the separation column. By using the pre-focusing column, impurities are removed from a sample solution and the specimen is condensed in the sample solution.

Inside the pre-focusing column, a column packing material corresponding to the specimen to be analyzed is provided, such that the sample solution is condensed by the foregoing column packing material.

Thus, the separation process in the separation column is made based on the condensed specimen solution, and the performance of separation in the separation column is improved significantly.

The use of a small-volume, semi-micro column for the purpose of pre-focusing column is particularly advantageous for improving the efficiency of condensation therein and hence for improving the performance of separation in the separation column.

On the other hand, a specimen to be analyzed generally contains a wide variety of impurities, and there can be a case in which the efficiency of condensation in the pre-focusing column is seriously deteriorated.

For example, the use of a liquid chromatograph for separating a mixture containing a blood serum causes a problem in that proteins contained in the blood serum with a large amount are adsorbed on the column packing material and the efficiency of condensation is impaired.

In order to avoid the problem of degrading of condensation in the column packing material and to secure a high resolution separation in the separation column, it has been necessary to remove the proteins from the specimen prior to the process of liquid chromatography by conducting a preparation process.

However, such a preparation process takes a time and a substantial work load. Further, such a preparation process tends to cause a degradation in the precision of analysis. In view of above, there are provided new column packing materials that allow a direct injection of specimen containing proteins into the liquid chromatograph without conducting the process of removing the proteins. The column packing material thereby achieves the condensation of the protein-containing specimen.

These improved column packing materials use porous glass or silica gel as a carrier, and a substance having a different property is provided on the surface of the pores. By using such an improved column packing material, the large protein molecules are refused to enter the fine pores. The large protein molecules merely pass through the column without being adsorbed on the hydrophilic surface (surface outside the pores), while small molecules of drugs are adsorbed by the hydrophobic inner surface (pore inner surface).

An example of such a column packing material is disclosed in the Japanese Laid-Open Patent Publication 60-56256. In the foregoing reference, the column packing material has a protein coating on a silica surface to which an octadecyl group is bonded. The protein used for the coating may be a bovine serum albumin, and the packing material is formed by adsorption and denaturation of the protein on the octadecyl-bonded silica surface.

On the other hand, such a protein-coated ODS silica packing material has a drawback in that the adsorbed denaturation protein tends to cause an elution when used for a long time. Further, such a packing material has a problem of durability or resolution in that it is difficult to provide a column of high separation efficiency.

In order to improve the foregoing problems, it is proposed, as described in the Japanese Laid-Open Patent Publications 61-65159 and 1-123145, to provide a method of producing a column packing material according to the steps of:

(1) introducing hydrophobic groups on the inner surface and outer surface of the porous support;

(2) selectively disconnecting the hydrophobic groups from the outer surface by using an enzyme, which is a macromolecules and cannot enter the pores of the silica support; and then (3) introducing hydrophilic groups on the outer surface.

In more detail, the Japanese Laid-Open Patent Publication 61-65159 describes a process of: bonding oligopeptide on a porous silica as a starting material to which a glycerylpropyl group is introduced, via carbonyldiimidazole; and disconnecting the phenylalanine side chain on the outer surface by a hydrolysis using carboxypeptidaze A as a proteolytic enzyme. As a result of this, glycol-phenylalanylphenylalanine remains on the inner surface of the column packing material as a hydrophobic ligand, while the outer surface carries a hydrophilic glycyl-glycerylpropyl group thereon.

According to the process of the Japanese Laid-Open Patent Publication 1-123145, there is described a process of: introducing a hydrophobic group on the surface of a porous silica starting material, to which an aminopropyl group is introduced, via an amide bond, by causing a reaction with octanoyl chloride under existence of triethylamine; causing a hydrolysis in the acyl group on the surface by using polymyxin acylase; and making the amino group on the outer surface to be hydrophilic by conducting a reaction with glycydol.

When the foregoing column packing material disclosed in the Japanese Laid-Open Patent Publication 61-65159 or 1-123145 is used for the pre-focusing column of a liquid chromatograph, on the other hand, there arises a problem, associated with the fact that the disclosed packing materials are formed by using an enzyme reaction, in that the production of the column packing material is complicated and the obtained column packing material tends to show a variation in the performance.

Further, there has been a problem in the conventional liquid chromatograph, which uses a pre-focusing column of large volume of 2.0 ml or more, in that the specimen supplied thereto may be diluted rather than condensed. When this occurs, the precision of detection is deteriorated inevitably. This problem becomes particularly serious in the case in which the amount of the injected specimen is very small.

It should be noted that the foregoing packing materials have a common feature of removing a substance such as proteins. In order to remove proteins selectively, the surface of the foregoing conventional packing materials is controlled hydrophobic or hydrophilic. On the other hand, such a control does not enhance the separation effect of the specimen to be analyzed.

Thus, the specimen to be analyzed is still processed by the hydrophobic surface in the foregoing conventional packing material just similarly as before, and thus, the type of the specimens, particularly the range of the specimens subjected to the pre-focusing condensation process, is essentially the same as in the conventional case.

Thus, the specimen to be condensed is limited, in the foregoing prior art, to a non-polar or low-polar substance, and the prior art cannot achieve an effective pre-focusing condensation process for ionic substances contained in a biological specimen. This problem occurs when the prior art process is applied to the analysis of a biological specimen, which may be a mixture of various substances including blood serum.

The present invention is made in view of above and has an object to provide a liquid chromatograph using a small-volume pre-focusing column which is easy to make and provides a high efficiency of condensation.

Another object of the present invention is provide a liquid chromatograph and a method of analysis, wherein a packing material having a function of cation exchange is used for the packing material of the pre-focusing column and for the packing materials of the pre-focusing column and the separation column, so that a high efficiency of resolution is achieved for the cationic substances in the specimen analyzed.

DISCLOSURE OF THE INVENTION

According to the invention of claim 1, there is provided a liquid chromatograph, comprising:

a separation column for separating a specimen supplied thereto together with a solvent by a pump for analysis;

flow-path control means disposed between said pump and said separation column, said flow-path control means being supplied with said solvent from said pump and said specimen from a specimen injection tube, said flow-path control means supplying said solvent to said separation column together with said specimen;

detection means supplied with said specimen separated by said separation column, said detection means analyzing said specimen;

a specimen holding mechanism holding a plurality of vessels each containing a specimen to be analyzed;

specimen injection means sampling a specimen selectively from one of said plurality of vessels, said specimen injection means supplying said sampled specimen to said flow-path control means; and a pre-focusing column provided between said flow-path control means and said separation column, said pre-focusing column condensing said specimen that is supplied together with said solvent;

said pre-focusing column having a volume of less than 2.0 ml, said pre-focusing column being packed with a column packing material of a porous support coated by a silicone polymer having a Si—R—X bond (R represents a spacer part, X represents a sulfonic group) and a Si—R' bond (R' represents a hydrophilic group).

According to the invention of claim 2, there is provided a liquid chromatograph as claimed in claim 1, wherein the hydrophilic group R' is a hydrophilic group containing a hydroxyl group.

According to the invention of claim 3, there is provided a liquid chromatograph as claimed in claim 1, wherein the spacer part R of said column packing material is formed of a hydrocarbon residue containing 1–40 carbon atoms or a substituent of said hydrocarbon residue in which said carbon atoms are partially substituted by an oxygen atom or a nitrogen atom.

According to the invention of claim 4, there is provided a liquid chromatograph as claimed in any of claim 1, wherein said porous support constituting said packing material packed in said pre-focusing column is a silica gel.

According to the invention of claim 5, there is provided a liquid chromatograph as claimed in claim 1, wherein said separation column has a volume of less than 2.0 ml, and wherein said separation column is a cation-exchange column packed with an ion-exchange packing material having a cation-exchange function.

According to the invention of claim 6, there is provided a method of analysis, comprising the steps of:

supplying a specimen dispersed in a solvent, to a pre-focusing column, said pre-focusing column including a column body having a volume of less than 2.0 ml and filled with a porous support coated by a silicone polymer, said silicone polymer having a Si—R—X bond (R represents a spacer part, X represents a sulfonic group) and a Si—R' bond (R' represents a hydrophilic group) and condensing said specimen dispersed in said solvent;

supplying said condensed specimen to a separation column for separating said specimen dispersed in said solvent; and analyzing said separated specimen by detection means.

According to the invention of claim 7, there is provided a method of analysis, comprising the steps of:

supplying a solvent acting as a mobile phase to a flow-path control device by a pump and further supplying a specimen to said flow-path control device via a specimen injection tube connected to said flow-path control device, said flow-path control device thereby dispersing said specimen in said solvent;

supplying said specimen dispersed in said solvent to a pre-focusing column according to a pumping pressure of said pump exerted on said solvent, said pre-focusing column being packed with a packing material for condensing said specimen;

condensing said specimen by said pre-focusing column;

supplying said condensed specimen to a separation column according to a pumping pressure of said pump exerted on said solvent, said separation column separating said specimen dispersed in said solvent;

supplying said separated specimen to detection means according to a pumping pressure of said pump exerted on said solvent for analyzing said specimen, said pre-focusing column having a volume of less than 2.0 ml, said pre-focusing column being packed by a column packing material of a porous support coated by a silicone polymer, said silicone polymer having a Si—R—X bond (R represents a spacer part, X represents a sulfonic group) and a Si—R' bond (R' is a hydrophilic group).

According to the intention of claim 8, there is provided a method as claimed in claim 7, wherein said separation column has a volume of less than 2.0 ml and wherein an ion-exchange packing material having a cation-exchange function is packed in said separation column.

According to the invention of claim 9, there is provided a method of analyzing a cationic compound in a biological specimen, by applying a method of analysis of claim 7 or 8 to said biological specimen that contains said cationic compound.

According to the invention of claim 10, there is provided a method of analyzing a biological specimen containing a cationic compound and a protein, by applying a method of analysis of claim 7 or 8 for analyzing said cationic substance in said biological specimen.

According to the invention of claim 11, there is provided a method of analyzing a biological tissue specimen acquired from any of blood plasma, blood serum, urine, saliva and a biological tissue, by applying a method of analysis as claimed in claim 7 or 8 to said biological tissue specimen as said specimen, such that a cationic substance in said specimen is analyzed.

According to the invention of claim 12, there is provided a column packing material comprising a porous support coated by a silicone polymer, said silicone polymer having a Si—R—X bond (R represents a spacer part, X represents a sulfonic group) and a Si—R' bond (R' represents a hydrophilic group).

According to the invention of claim 13, there is provided a column packing material as claimed in claim 12, wherein said hydrophilic group R' of said Si—R' bond is a hydrophilic group having a hydroxyl group.

According to the invention of claim 14, there is provided a column packing material as claimed in claim 12, wherein said spacer part R of said Si—R—X bond is formed of a hydrocarbon residue containing 1–40 carbon atoms or a substituent of said hydrocarbon residue in which said carbon atoms are partially substituted by oxygen atoms or nitrogen atoms.

According to the invention of claim 15, there is provided a column packing material as claimed in any of claim 12, wherein said porous support constituting said packing material is a silica gel.

According to the features of claims 1, 2 and 3, the problem of dilution of the specimen is successfully avoided by reducing the volume of the pre-focusing column of the liquid chromatograph to be less than 2.0 ml, and the condensation process proceeds reliably in the pre-focusing column. Dilution does not occur even when the amount of the specimen to be injected is small. Associated with this, the chromatograph of the present invention can provide a precise analysis.

In the present invention, the column packing material in the pre-focusing column comprises a porous support coated by a silicone polymer having a Si—R—X bond (R represents a spacer part, X represents a sulfonic group) and a Si—R' bond (R' represents a hydrophilic group). In such a column packing material, a part of the outer surface thereof is hydrophilic, and thus, the problem of adsorption of proteins contained in a biological specimen does not occur even when the liquid chromatograph is used for a biological specimen. Further, the packing material is stable and provides a superior resolution, and the condensation of the specimen is achieved reliably. As no enzymes are used for the reaction, the packing material of the present invention shows an excellent reproducibility and the condensation process can be achieved with reliability.

In addition, it should be noted that the sulfonic group provided at the tip end of the spacer part R shows strong ionic interaction with cations. Thus, the column packing material has a cationic exchange function and is capable of condensing cationic compounds selectively.

Thus, the liquid chromatography of the present invention provides an excellent resolution for cationic compound specimens.

According to the feature of claim 4, a silica gel is used for the packing material packing the pre-focusing column, wherein the use of silica gel is advantageous in the point that it is free from the problem of swelling by the solvent, which is used for the mobile phase.

Thus, the liquid chromatography of the present invention provides an excellent resolution for the cationic compound specimens. Further, the reliability of analysis is improved substantially.

According to the feature of claim 5, the specimen is condensed by utilizing the cationic nature of the specimen. The specimen is then subjected to a separation process by further utilizing the cationic nature thereof.

Thus, the liquid chromatography of the present invention provides an excellent resolution for the cationic compound specimens.

According to the features of claims 6 and 7, the problem of dilution of the specimen is successfully avoided by reducing the volume of the pre-focusing column of the liquid chromatograph to be less than 2.0 ml, and the condensation process proceeds reliably in the pre-focusing column. Associated with this, the chromatograph of the present invention can provide a precise analysis.

In the present invention, the column packing material in the pre-focusing column comprises a porous support coated by a silicone polymer having a Si—R—X bond (R represents a spacer part, X represents a sulfonic group) and a Si—R' bond (R' represents a hydrophilic group). In such a column packing material, a part of the outer surface thereof is hydrophilic, and thus, the problem of adsorption of proteins contained in a biological specimen does not occur even when the liquid chromatograph is used for a biological specimen. Further, the packing material is stable and provides a superior resolution, and the condensation of the specimen is achieved reliably. As no enzymes are used for the reaction, the packing material of the present invention shows an excellent reproducibility and the condensation process can be achieved with reliability.

In addition, it should be noted that the sulfonic group provided at the tip end of the spacer part R shows strong ionic interaction with cations. Thus, the column packing material has a cationic exchange function and is capable of condensing cationic compounds selectively.

Thus, the liquid chromatography of the present invention provides an excellent resolution for cationic compound specimens.

According to the feature of claim 8, the specimen is condensed by utilizing the cationic nature of the specimen. The specimen is then subjected to a separation process by further utilizing the cationic nature thereof.

Thus, the liquid chromatography of the present invention provides an excellent resolution for the cationic compound specimens.

According to the features of claims 9, 10 and 11, it becomes possible to concentrate the cationic compound contained in a biological specimen by utilizing the cationic nature of the compound.

Further, the operation of the cationic compound can be achieved by utilizing the cationic nature of the compound.

Thus, the present invention enables analysis of a biological specimen, particularly a cationic compound contained therein, with excellent resolution and separation.

According to the feature of claims 12, 13 and 14, the column packing material of the present invention has a Si—R—X bond, with a sulfonic group bonded to a tip end of the spacer part R. As the sulfonic group exhibits a strong ionic interaction to cations, the column packing material of the present invention shows a cation-exchange function, which enables the column packing material to selectively hold or concentrate cationic compounds.

Thus, the column packing material of the present invention shows a high performance in concentrating cationic specimens.

Further, because of the presence of the Si—R' bond, a part of the outer surface of the column packing material of the present invention is hydrophilic in nature. Thus, the problem of adsorption of proteins is successfully avoided even when the column packing material of the present invention is used for a biological specimen that contains proteins. Further, the packing material of the present invention is stable and has an excellent resolution, and thus, it is possible to carry out the concentration with reliability by using the column packing material.

From the foregoing, it is possible to provide, according to the present invention, a stable and high-performance column packing material, which is applicable to biological specimens such as a cationic compound containing proteins.

According to the invention of claim 15, it is possible to use silica gel for the porous support of the column packing material for use in the pre-focusing column, wherein silica gel is a reliable material free from the problem of swelling, which tends to be caused by the solvent used for the mobile phase in liquid chromatography.

Thus, the present invention provided a reliable column packing material having an excellent retention performance, and hence concentration performance, for cationic specimen compounds.

BEST MODE OF IMPLEMENTING THE INVENTION

Hereinafter, preferred embodiments of the present invention will be described.

Figure 1:
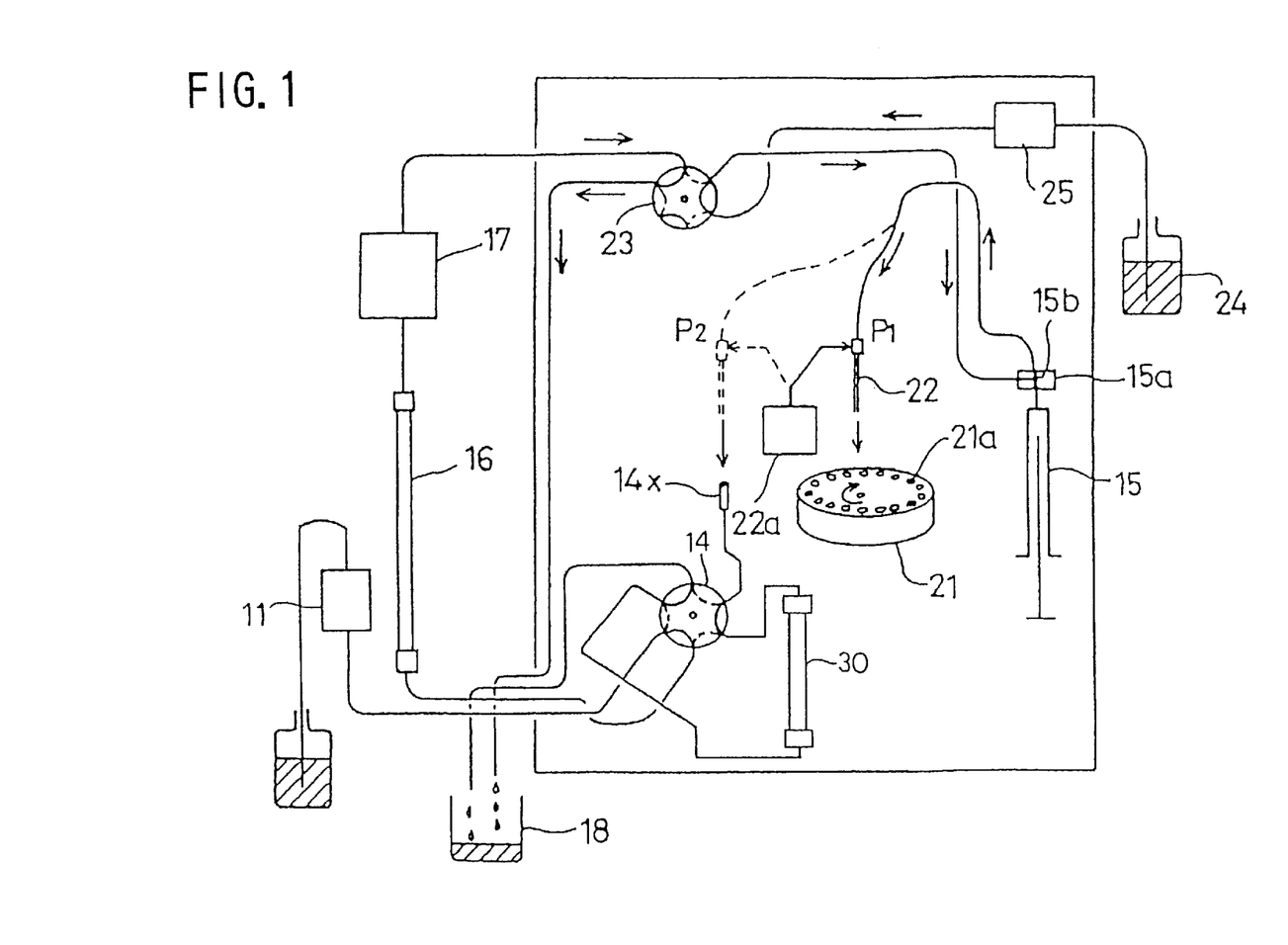
FIG. 1 is a diagram showing the general construction of a liquid chromatograph according to a first embodiment of the present invention.
Figure 2:
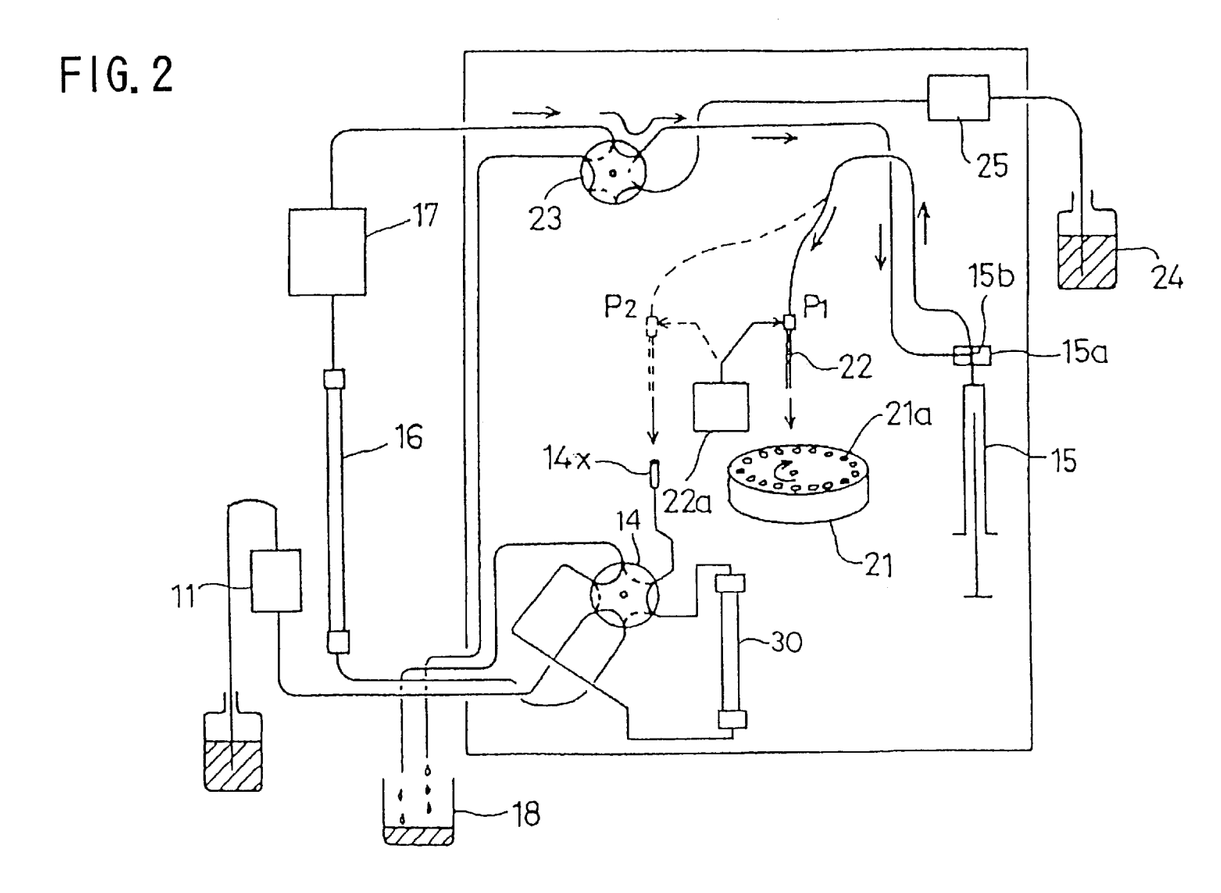
FIG. 2 is a diagram explaining the operation of the liquid chromatograph of the first embodiment of the present invention.
Figure 3:
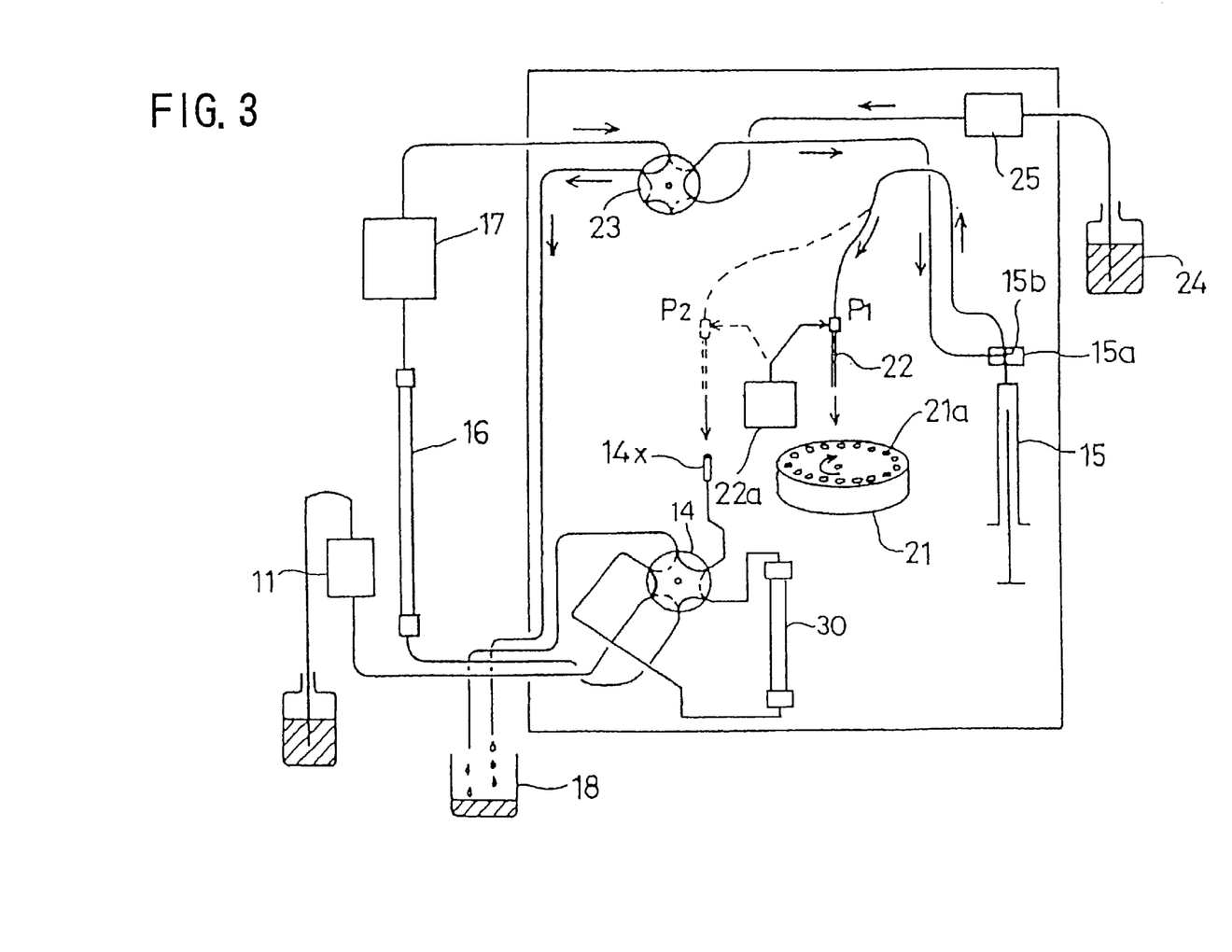
FIG. 3 is another diagram explaining the operation of the liquid chromatograph of the first embodiment of the present invention.

FIGS. 1–3 show the general construction of the liquid chromatograph according to a first embodiment of the present invention.

Referring to the drawings, the liquid chromatograph according to the embodiment of the present invention includes a specimen holding part 21 in which a plurality of specimen vessels 21a are formed, wherein each of the specimen vessels 21a holds therein the specimen to be analyzed. Typically, each specimen vessel 21a has a volume of about 250 μl. Further, the liquid chromatograph includes a specimen injection tube 22 held movably by a robot 22a, wherein the specimen injection tube 22 is moved to a position $P_1$ by the action of the robot 22a, followed by a downward movement, and thus, the specimen injection tube 22 is inserted into one of the plurality of specimen vessels 21a. After this, a syringe 15 cooperating with the specimen injection tube 22 is actuated and the tube 22 sucks the specimen held in the vessel 21a.

Further, the liquid chromatograph includes a six-port valve 14 as a first switching valve, wherein an acceptor 14X for accepting the tip end of the specimen injection tube 22 is connected to the first switching valve 14. Further, the first switching valve 14 is connected to a pre-focusing column 20, which constitutes the essential part of the present invention.

It should be noted that the pre-focusing column 30 is a small-sized column having a volume of less than 2.0 ml and is filled with the column packing material to be described later. The pre-focusing column 30 carries out condensing of the specimen supplied thereto, and thus, the specimen thus condensed is supplied to a separation column 16 and to a detector 17 to be described later. Thereby, the precision of the analysis is improved substantially.

In the foregoing construction, the acceptor 14X is used for an injection port of the specimen to be analyzed. Thus, the specimen taken up by the specimen injection tube 22 is injected into the acceptor 14X by inserting the specimen injection tube 22 into the acceptor 14x and by actuating the syringe 15 once again.

In this procedure, the specimen injection tube 22 is moved laterally to a position $P_2$ corresponding to the end 14X by the robot 22a, followed by a vertical movement for insertion into the acceptor 14X. The specimen solution thus injected by the specimen injection tube 22 is forwarded to the pre-focusing column 30 for condensation when the fist switching valve 14 is in the state as represented in FIG. 1 and FIG. 2.

In the liquid chromatograph of the present embodiment, it should further be noted that another six-port valve 23 is connected to a specimen outlet port of the detector 17 as a second switching valve. This second switching valve 23 acts to supply the separated specimen, which is ejected after the separation process in the separation column 16 and detection process in the detector 17, to either a waste reservoir 18 or the specimen injection tube 22 selectively. In the state shown in FIG. 1 or FIG. 3, the specimen separated and ejected from the detection 17 is forwarded to the waste reservoir 18.

In the case of sending back the specimen thus separated again to the tube 22, the separated specimen is supplied to the specimen injection tube 22 via a flow-path 15b provided in a joint 15a, which joint 15a being provided on the syringe 15. It should be noted that the flow-path 15b has a T-shaped form such that any of the specimen supplied by the syringe 15 and the specimen supplied by the valve 23 is forwarded to the specimen injection tube 22.

Further, it should be noted that the illustrated liquid chromatograph includes, in addition to the separation column 16, a vessel 24 cooperating with the separation column 16 and holding a cleaning solution for cleaning the piping of the liquid chromatograph, wherein the cleaning solution is supplied to the second switching valve 23 from the vessel 24 via a pump 25. In the state of FIG. 1 and FIG. 3, the cleaning solution is supplied to the specimen injection tube 22 via the joint 15a and cleans the tube 22. When cleaning the specimen injection tube 22, the robot 22a moves the needle 22 to a waste recovery position (not illustrated), which is different from any of the position $P_1$ or $P_2$.

FIG. 2 shows the state in which the second switching valve 23 is rotated in the liquid chromatograph of FIG. 1. In the illustrated state, the specimen ejected from the detector 17 after separation is caused to flow through the valve 23 as indicated by an arrow, and reaches the needle 22 via the flow-path 15b in the joint 15a. On the other hand, the cleaning liquid from the vessel 24 is blocked by the second switching valve 23. As a result of this, the specimen ejected from the detector 17 is recovered by a suitable specimen vessel 21a of the specimen holding part 21 by moving the specimen injection tube 22 to a position corresponding to the foregoing specimen vessel 21a.

When using a semi-micro column having a column inner diameter of 1.0–2.0 mm for the chromatograph separation column 16, in particular, the total flow rate of the solvent is very small, 50–200 $\mu$l/min at best. Thus, a vessel having a volume of several hundred milliliters is sufficient for the specimen vessel 21a when recovering the separated specimen into the specimen vessel 21a, even when the increase of volume of the specimen caused by dilution by the solvent is taken into consideration.

FIG. 3 shows the state in which the first switching valve 14 is rotated. In the illustrated state, the supply of the specimen from the acceptor 14X to the supply port of the pre-focusing column 30 is blocked by the valve 14, and the pre-focusing column 30 is supplied with the solvent at the foregoing supply port by the pump 11. Further, in the state of FIG. 3, the ejection port of the pre-focusing column 30 is connected to the separation column 16. Thus, the specimen condensed by the pre-focusing column 30 is supplied to the separation column 16 for separation, and the specimen separated by the separation column 16 is supplied to the detector 17 for a predetermined analysis.

Figure 4:
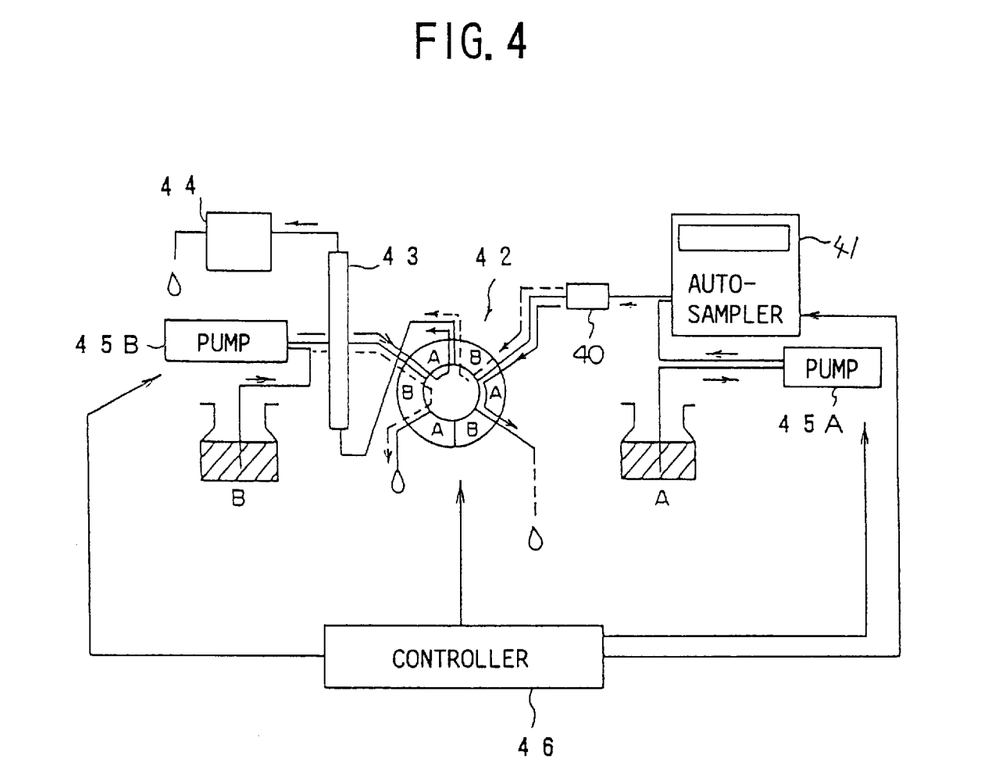
FIG. 4 is a diagram showing the general construction of a liquid chromatograph according to a second embodiment of the present invention.

FIG. 4 shows the construction of a liquid chromatograph according to a second embodiment of the present invention.

Referring to FIG. 4, the liquid chromatograph of the present embodiment includes a pre-focusing column 40 disposed between an automatic sampler 41 and a 6-valve switching valve 42 (referred to hereinafter as "switching valve") formed of a six-port valve for first stage separation.

It should be noted that the pre-focusing column 40 is a small column having a volume of less than 2.0 ml and is packed with the column packing material to be described later, similarly to the pre-focusing column 30 of the liquid chromatograph of the first embodiment. The pre-focusing column 40 carries out the condensation of the specimen supplied from the automatic sampler 41, and a condensed specimen is supplied from the pre-focusing column 40 to the separation column 43 and the detector 44. Thereby, the precision of analysis is improved substantially.

Further, the liquid chromatograph of the present embodiment includes the switching valve 14, syringe 15 and the specimen injection tube 22 in the automatic sampler 41, together with other related elements. Further, the pumps 45A and 45B form together a specimen feeding system that supplies the specimen to be analyzed to the pre-focusing column 40, separation column 43 and further to the detector 44 in cooperation with the switching valve 42.

According to the construction of FIG. 4, the specimen to be analyzed is supplied, together with the solvent (mobile phase A) from the pump A, to the pre-focusing column 40 from the automatic sampler 41 for condensation. The specimen thus condensed in the pre-focusing column 40 is then supplied, together with a solvent (mobile phase B) supplied from the pump 45B, to the separation column 43 for separation. Thereby, the switching between the mobile phase A and the mobile phase B is achieved by the switching valve 42.

The specimen thus transported is subjected to a separation process in the separation column 43, and then a detection process in the detector 44. Further, it should be noted that the liquid chromatograph of the foregoing construction includes a controller 46 for controlling the analysis process, wherein the controller 46 controls the driving of the automatic sampler 41, switching valve 42 and the pumps 45A and 45B.

Further, the liquid chromatograph of the foregoing type having the two-column construction is advantageous over ordinary liquid chromatograph in the point that the two-column liquid chromatograph of the two-column construction is capable of eliminating the treatment to the specimen to be analyzed. Thus, the two-column liquid chromatograph is used commonly as a sample-treatment-free system.

Next, the operation of the switching valve 42 conducted under control of the controller 46 will be described. It should be noted that the switching valve 42 switches the flow-path formed in the liquid chromatograph under control of the controller 46 between a first state and a second state.

In the first state of the switching valve 42, the specimen pumped from the automatic sampler 41 under the pumping pressure of the pump 45A is supplied, after passing through the pre-focusing column 40, to the switching valve 42 and further to the waste reservoir not illustrated along the line represented in the drawing by a continuous line. In this process, the substance contained in the specimen and is subjected to the analysis is selectively captured by the pre-focusing column 40 and is condensed therein. Further, the mobile phase B is pumped to the switching valve 10 by the pump 45B and is supplied to the separation column 43 along the line indicated in FIG. 4 by a continuous line.

When the switching valve 42 causes a transition to the second state under control of the controller 46, on the other hand, the specimen condensed in the pre-focusing column 40 is supplied to the separation column 43 for analysis by causing a flow along a broken line shown in FIG. 4. On the other hand, the mobile phase B supplied by the pump 45B is caused to flow to the waste reservoir not illustrated along a broken line indicated in FIG. 4.

Hereinafter, a description will be made on the packing material used to fill the pre-focusing column 30 or 40. In the present embodiment, a column packing material formed of a porous support coated with a silicone polymer is used wherein the silicone polymer has a Si—R—X bond (R represents a spacer part, X represents a sulfonic group) and a Si—R' bond (R' represents a hydrophilic group). By using the column packing material of the foregoing construction, it is possible to enhance the resolution of proteins when the liquid chromatograph is used for the analysis of a blood serum which contains proteins. Thus, a reliable and stable condensation becomes possible by using the column packing material of the present invention. Hereinafter, a more detailed description will be made on the column packing material used in the present embodiment.

In the present embodiment, the porous support is selected from a group of powdery materials used commonly for the support of packing material in the art of liquid chromatography, such as: silica gels; alumina; glass beads (porous glass beads, for example); zeolites; hydroxy apatites; or graphites. Further, the use of composite powders may be possible. In such composite powders, the surface of a synthetic resin, which may be polyamide, an acrylic resin or polyvinylalcohol, is covered by fine inorganic powders of silica gel, titanium dioxide or hydroxy apatite.

It is preferable to use the porous support having the average diameter of 2–200 μm and a specific surface area of 200–300 m²/g, with the pores of 40–120 Å diameter. More preferably, the porous carrier may be those formed of spherical-shaped or crushed silica gel particles having a grain size of 3–50 μm and a specific surface area of 400–600 m²/g, with the pores having a diameter of 60–80 Å.

It should be noted that the present invention uses at least one silicone compound having a Si—H group and represented by the general formula I below:

$$(R^1HSiO)_a(R^2R^3SiO)_b(R^4R^5R^6SiO_{1/2})_c \qquad \text{Eq. (I)}$$

(wherein each of $R^1$, $R^2$ and $R^3$ is a hydrogen atom or a hydrocarbon radical having 1–10 carbon atoms substituted by at least one halogen atom, excluding the case of $R^1$, $R^2$ and $R^3$ are all formed of a hydrogen atom. Each of $R^4$, $R^5$ and $R^6$ is a hydrogen atom or a hydrocarbon radical having 1–10 carbon atoms substituted by at least one halogen atom. Further, a is 0 or an integer equal to or larger than 1, b is 0 or an integer equal to or larger than 1, and c is 0 or 2, wherein the sum of a and b becomes an integer equal to or larger than 3 when the value of c is zero).

It should be noted that the foregoing silicone compound of Eq. I includes two groups, in which the first group corresponds to the case of c=0 in Eq. I. More specifically, the first group is a cyclic silicone compound having a general formula of:

$$(R^1HSiO)_a(R^2R^3SiO)_b \qquad \text{Eq. (II)}$$

(wherein $R^1$, $R^2$, $R^3$, a and b are identical with the case of Eq. I. Preferably, each of $R^1$, $R^2$ and $R^3$ is a hydrocarbon radical having 1–10 carbon atoms substituted by at least one halogen atom, the sum of a and b is 3 or more).

A representative examples of this compound are as follows:

Eq. (III)

(where n is an integer of 3–300).

Eq. (IV)

(where a + b = 3–300).

The compounds of Eq. (III) or Eq. (IV) can be used alone or in the form of mixture.

In each of Eqs. (III) and (IV), it should be noted that the value of n (or a+b) is preferably 3–7. With decreasing value of n, the boiling point of the compound decreases. Thereby, the amount of the compound that is deposited on the carrier as a vaporization process increases. Particularly, the trimer or tetramer is suitable in view of easiness of polymerization due to the stereoscopic nature of the compound.

The cyclic silicone compound of Eq. (II) includes dihydrogenhexamethylcyclotetrasiloxane, trihydrogenpentamethylcyclotetrasiloxane, tetrahydrogenpentamethylcyclotetrasiloxane, dihydrogenoctamethylcyclopenta siloxane, trihydrogenheptamethylcyclopentasiloxane, tetrahydrogenhexamethylcyclopentanesiloxane, and pentahydrogenpentamethylcyclopentasiloxane, and the like.

On the other hand, the second group of Eq. (I) corresponds to the case of the compound of Eq. (I) in which c is set equal to 2 (c=2) and includes the silicone compound represented by the general formula V below:

$$(R^1HSiO)_a(R^2R^3SiO)_b(R^4R^5(SiO_{1/2})_c \qquad \text{(Eq. V)}$$

(where $R^1$, $R^2$, $R^3$, $R^4$, $R^5$, $R^6$, a and b are identical to those define before, and the parameter c is set equal to 2). Preferably, each of $R^1$–$R^6$ is a hydrocarbon group having 1–10 carbon atoms which may be replaced by at least one halogen atom. A representative example of this compound is represented by the general formula VI below:

Eq. (VI)

(where n is an integer of 2–100).

The normal chain silicone compound of the formula of Eq. (V) includes the compounds of 1,1,1,2,3,4,4,4-octamethyltetrasiloxane, 1,1,1,2,3,4,5,5,5-nonamethylpentasiloxane, 1,1,1,2,3,4,5,6,6,6-decamethylhexasiloxane, and the like. The silicone compound represented by the general formula of Eq. (I) is contacted with the porous carrier in the vapor phase or liquid phase.

Spacer Part Having Sulfonic Group

It should be noted that the silicone polymer covering the surface of the support includes a spacer part having a sulfonic group, wherein the structure thereof is represented by the general formula:

$$(Si)—R_8—X \qquad (Eq. \text{ VII})$$

(wherein $R_8$ is: an alkyl group having a normal chain structure or a branched structure including 1–40 carbon atoms or a substituent thereof containing an oxygen atom or a nitrogen atom in which a part of the constituent carbon atoms of the foregoing alkyl group is replaced by the foregoing oxygen atom or nitrogen atom; or alternatively a cycloalkyl group or a cycloalkenyl group including 4–8 carbon atoms or a substituent of the cycloalkyl group or the cycloalkenyl group containing an oxygen atom or a nitrogen atom in which a part of the constituent carbon atoms of the foregoing alkyl group is replaced by the foregoing oxygen atom or nitrogen atom; or alternatively an aryl group, which may be substituted by 1–20 alkyl groups, or a substituent of the aryl group containing an oxygen atom or a nitrogen atom in which a part of the constituent carbon atoms of the aryl group is substituted by the oxygen atom or the nitrogen atom; or alternatively an alkyl group having a benzene ring structure or cycloalkane structure in a normal chain structure thereof and including 1–40 carbon atoms or a substituent thereof containing an oxygen atom or a nitrogen atom in which a part of the constituent carbon atoms of the foregoing alkyl group is replaced by the foregoing oxygen atom or nitrogen atom. X is a sulfonic group).

Hydrophilic Group

The packing material according to the present embodiment further includes —Si—R' (R' is a hydrophilic group) on the surface of the support coated by the silicone polymer. The hydrophilic group R' preferably includes therein a hydroxyl group, and thus, a substituent having a tetraol structure represented by the following formula is used:

Eq. (VIII)

Further, the polyol of the foregoing tetraol structure may also be used.

In the packing material thus obtained, a silica gel body is coated by the silicone polymer. Thus, the effect of silanol group on the silica gel is successfully covered and the problem of adsorption of the basic substance is avoided.

Figure 5A:
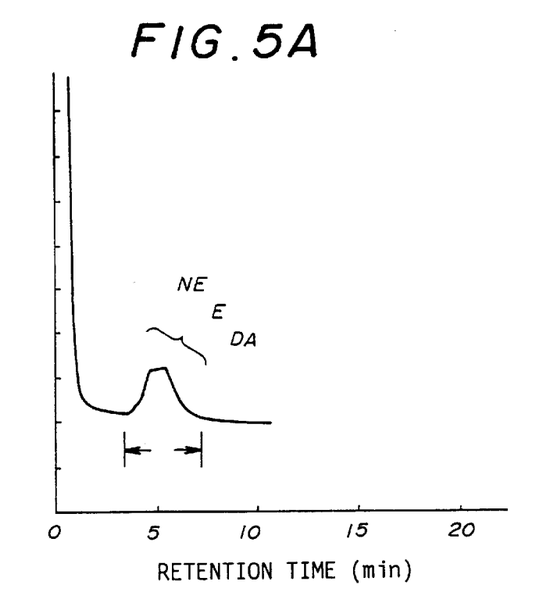
FIGS. 5A and 5B are chromatograms showing the retention performance of the column packing material according to an embodiment of the present invention as applied to a cationic substance.
Figure 5B:
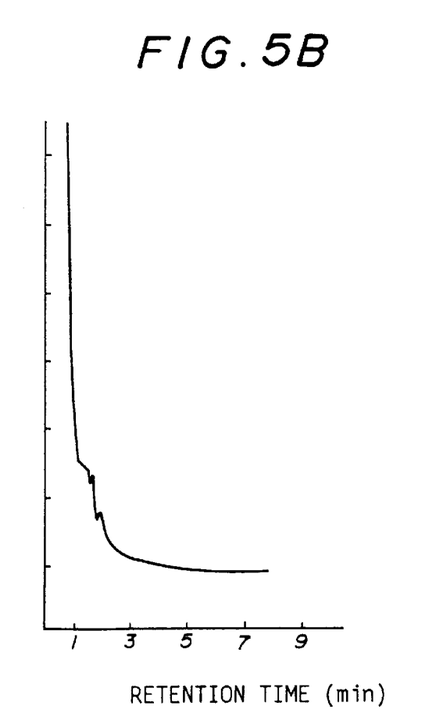

FIG. 5 shows the chromatogram indicating the retention characteristic of the column packing material of the present invention for a cationic substance.

In the experiment of FIG. 5, the column packing material is formed of a silica gel covered by a silicone polymer having a Si—R—X bond (R being a spacer part having a structure represented by the formula of Eq. (IX) below) and a Si—R' bond (R' being a hydroxyl group).

Eq (IX)

In the experiment, a silica gel powder of spherical silica gel particles having an average diameter of about 5 μm and pores of about 60 Å in diameter.

The column packing material was made according to the process described in the Japanese Laid-Open Patent Publication 8-262004 in combination with necessary chemical reactions.

The packing material according to the embodiment of the present invention was packed in a column having an inner diameter of 2.0 mm and a length of 10 mm, and a specimen containing catecholamine as a cationic substance (catecholamine is added to a blood serum with a concentration of 100 ppm) was introduced into the column. Further, the state of elution of catecholamine was examined based on the obtained chromatogram, and from this, the retention performance of the cationic substance is examined.

Following is the condition used for separation.
mobile phase: 10 μM EDTA-2Na 25 mmol/L phosphoric buffer solution (pH=6.9)
flow rate: 100 μL/min
separation temperature (column temperature): 35° C.
detection method: UV detection (254 nm)

For the purpose of comparison, a commercially available column packed with a conventional packing material (having a phenyl group on the surface) was also used for testing the retention performance of the specimen under the same separation condition.

FIG. 5A shows the chromatogram obtained by using the column packing material according to the embodiment of the present invention, while FIG. 5B shows the chromatogram obtained by conventional column packing material according to the comparative experiment.

As indicated in FIG. 5A, proteins in the blood serum are not retained and the proteins promptly cause an elution to a void volume of the column when the column packing material of the present embodiment is used. Thereby, catecholamines (norepinephrine (NE), epinephrine (E) and dopamine (D)) are held in the column and cause elution after the proteins have eluted.

In the comparative experiment, on the other hand, the catecholamines in the blood serum cause elution promptly from the column together with the proteins or solvent and are not retained in the column. Thereby, the chromatogram of the comparative experiment does not show the peak corresponding to the separated catechol amines.

From the foregoing, it was demonstrated that the column packing material according to the embodiment of the present invention does not retain proteins in blood serum, while the column packing material effectively retains cationic substances in the blood serum such as catecholamine. Thereby, the column packing material of the present invention effectively condenses the cationic substances.

Figure 6:
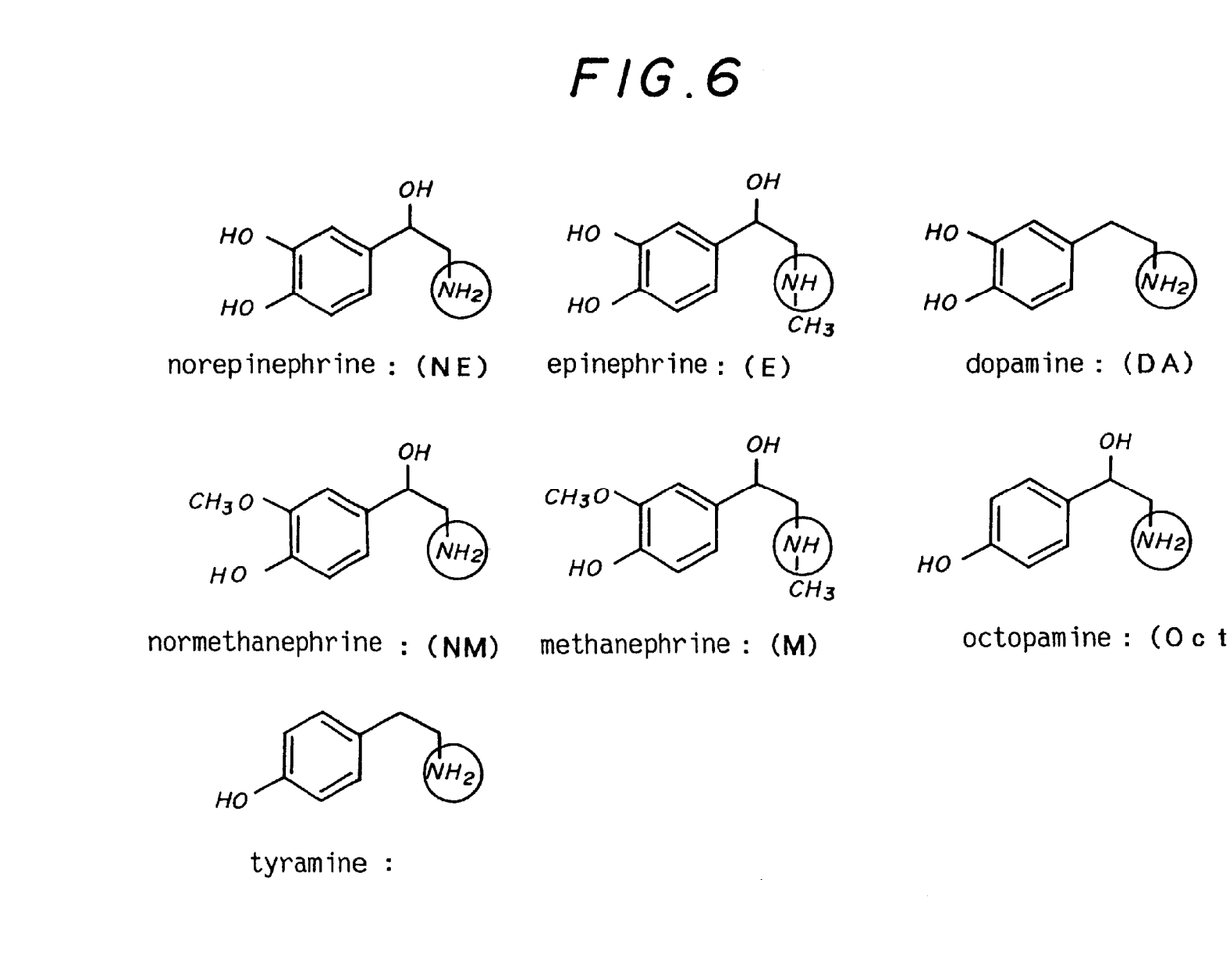
FIG. 6 is a diagram showing an example of the cationic substance which can be condensed by the column packing material according to an embodiment of the present invention.

It should be noted that the packing material according to the embodiment of the present invention holds and condenses not only catecholamines but also other various cationic substances represented in FIG. 6.

In this process, it is possible to adjust the retention characteristic by changing the salt concentration in the mobile phase.

Figure 7:
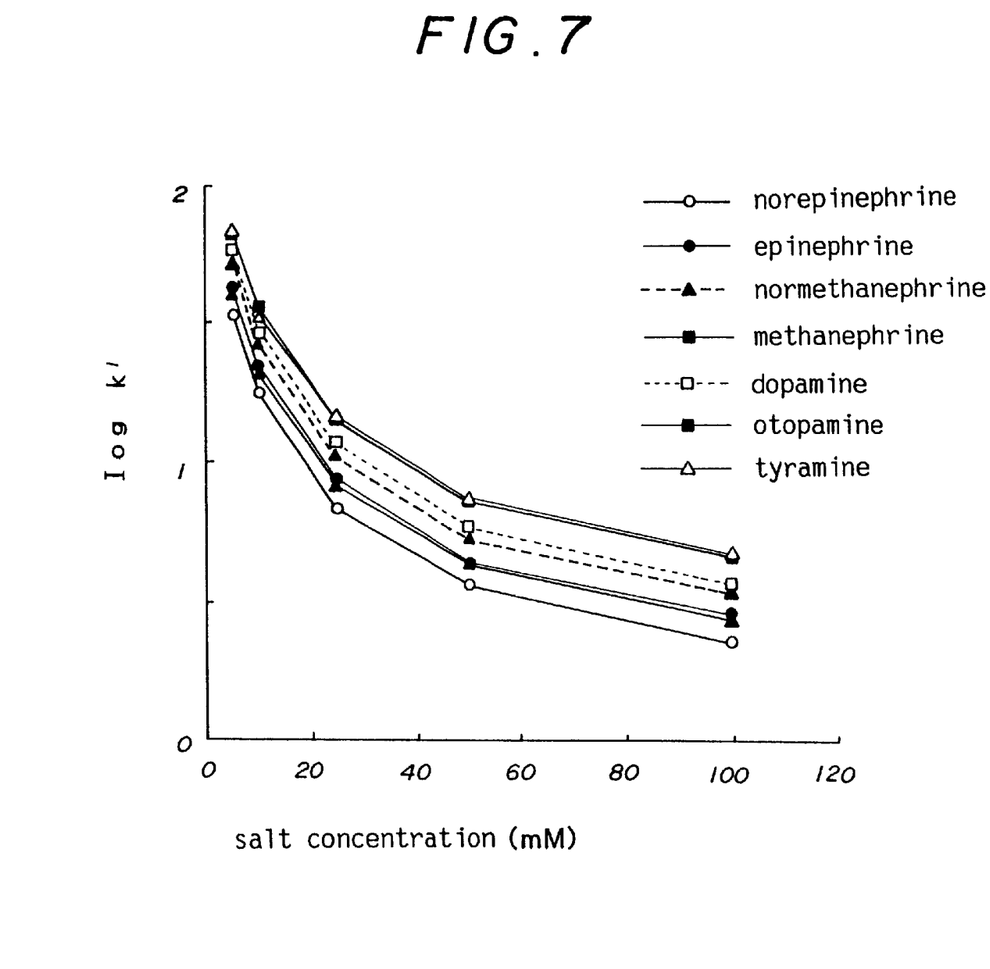
FIG. 7 is a graph showing the adjustment of retention, caused by a change of the salt concentration in the mobile phase, for the case in which the packing material according to the embodiment of the present invention is used.

FIG. 7 is a graph showing the change of retention characteristic of the packing material according to the embodiment of the present invention for the case in which the salt concentration in the mobile phase is changed. In FIG. 7, it should be noted that the vertical axis represents the retention ratio in logarithmic scale while the horizontal axis represents the salt concentration (mM).

Following is the condition used for separation.
column size: 2.0 mm i.d.×10 mm
separation temperature: 35° C.
mobile phase: phosphate buffer solution (pH=6.9)
salt concentration in the phosphate buffer solution: 5, 10, 25, 50 and 100 mM
flow rate: 0.1 ml/min
detection method: UV detection
specimen: solution containing cationic substances each with a concentration level of 100 ppm
amount of injected specimen: 2 µl As indicated in FIG. 7, the packing material according to the embodiment of the present invention is capable of adjusting the retention characteristic by using a mobile phase with various salt concentration levels for various cationic substances.

By using the packing material according to the present invention in the chromatograph of the present invention for the quantitative analysis of drugs or metabolites in a biological component such as a blood serum, particularly for the quantitative analysis cationic compounds, it becomes possible to eliminate the complicated preparation procedures, and the biological component can be injected directly.

Figure 8A:
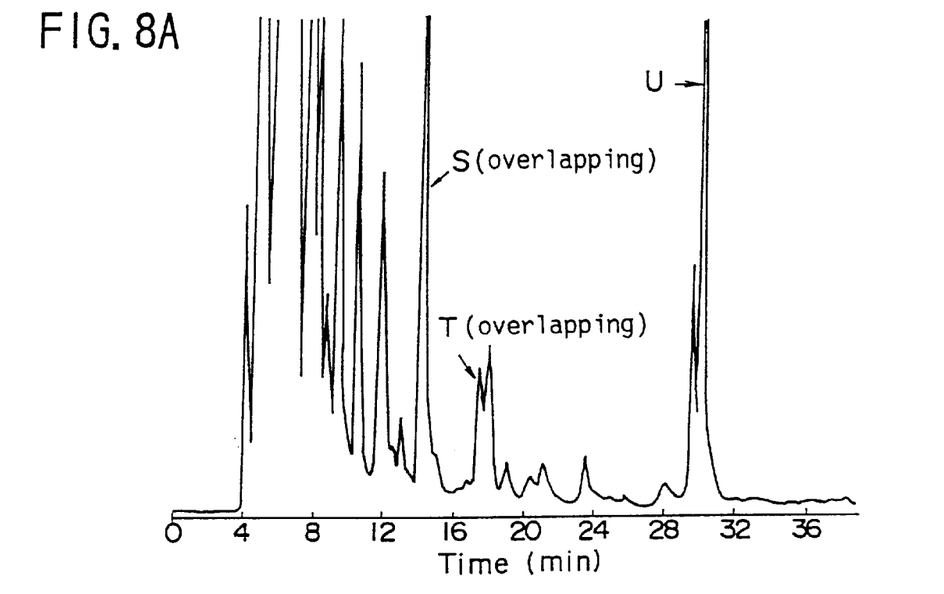
FIGS. 8A and 8B are chromatograms explaining the effect of the present invention.
Figure 8B:
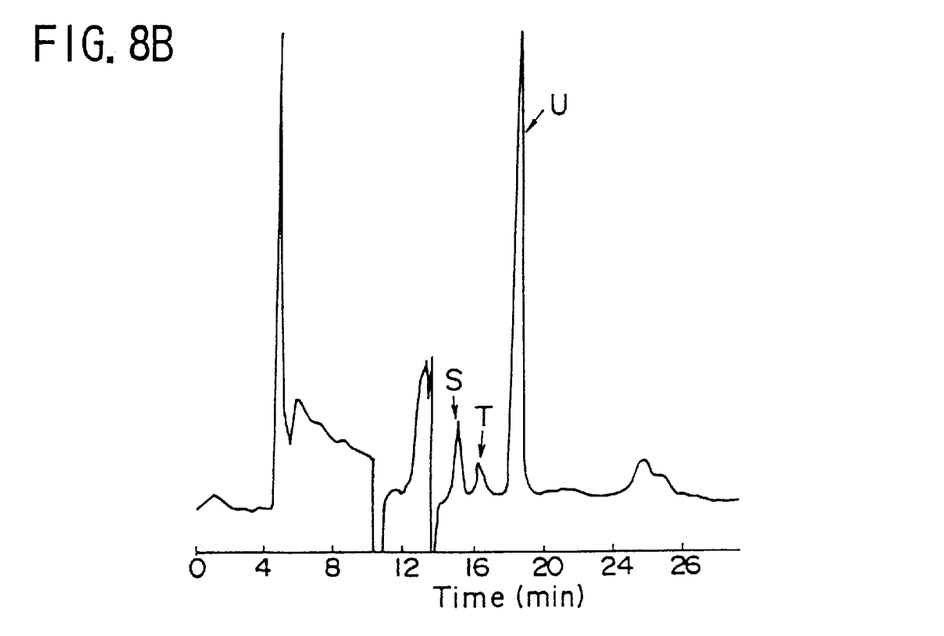

FIGS. 8A and 8B show the result of analysis experiments conducted by the liquid chromatograph of the present invention in which the column packing material described above was packed in the pre-focusing column 30 or 40, wherein FIG. 8A shows a comparative experiment in which a conventional column packing material was packed in the pre-focusing column 30 or 40. On the other hand, FIG. 8B shows the result wherein the column packing material according to the embodiment of the present invention described above was packed in the pre-focusing column 30 or 40.

In the comparative experiment of FIG. 8A, in which the column was packed by the conventional packing material, the same conventional packing material was used also for the separation column. In the experiment, the solvent for the mobile phase was selected such that an optimum separation is achieved for the target compound represented in the drawing by peaks S, T and U. In the condensation process, a 5 mM-buffered phosphoric acid/acetonitrile (=98/2) solution having a pH value of 6.0 was used. In the separation process, on the other hand, a 50 mM-phosphate buffer/acetonitrile (=94/6) solution containing 5 mM of sodium 1-octanesulfonate and having a pH value of 2.3 was used with a flow-rate of 0.1 ml/min.

The progress of the separation process was detected by an electrochemical detector.

In the analysis, 10 µl of human urine was used without any preparatory processing process.

FIG. 8B, on the other hand, shows the result in which the column packing material according to the embodiment of the present invention is packed in the pre-focusing column 30 or 40, in combination with a strong cation exchange column used for the separation column, wherein the strong cation exchange column has an inner diameter of 2.0 mm and a length of 150 mm.

In the experiment of FIG. 8B, too, an optimum selection for the mobile phase solvent was made such that an optimum separation is achieved for the target compound represented by the peaks S, T and U. In the condensation process, a 10 mM phosphate buffer solution having a pH value of 5.5 was used. In the separation process, on the other hand, a 100 mM phosphate buffer solution was used with a pH value of 3.0 and a flow rate of 0.2 ml/min.

The progress of the separation process was detected by an electrochemical detector.

In the experiment of FIG. 8B, 10 µl of human urine was used for the specimen, without any preparatory processing.

The result of the experiments can be evaluated from the degree of separation of the peaks S, T and U in the chromatogram obtained for the target compound.

As can be seen clearly in FIG. 8, the peaks S, T and U of the target compound are overlapping with the peaks of unnecessary compounds when the conventional column packing material is used. In this case, therefore, no satisfactory separation is achieved.

On the contrary, the experiment conducted by using the column packing material of the present embodiment provides a result in which the peaks S, T and U of the target compound appear sharply without overlapping, indicating that a satisfactory separation has been achieved.

The foregoing result of the present invention is achieved by the effect of the substituent having a sulfonic group and provided on the outer surface of the column packing material. Thus, the column packing material of the present invention can realize a stable condensation of target compounds, particularly cationic target compounds. As a result of the condensation, the separation in the chromatograph is improved and excellent analysis is achieved by using the column packing material of the present invention.

What is claimed is:

1. A liquid chromatograph for analyzing a specimen containing protein, comprising:

a separation column (16, 43) for separating a specimen supplied thereto together with a solvent by a pump (11, 45A) for analysis, said specimen containing protein molecules;

flow-path control means (14, 42) disposed between said pump (11, 45A) and said separation column (16, 43), said flow-path control means being supplied with said solvent from said pump and said specimen from a specimen injection tube (22, 41), said flow-path control means supplying said solvent to said separation column together with said specimen;

detection means (17, 44) supplied with said specimen separated by said separation column (16, 43), said detection means analyzing said specimen;

a specimen holding mechanism (21, 41) holding a plurality of vessels (21a) each containing a specimen to be analyzed;

specimen injection means (22, 41) sampling a specimen selectively from one of said plurality of vessels (21a), said specimen injection means supplying said sampled specimen to said flow-path control means (14, 42); and a pre-focusing column (30, 40) provided between said flow-path control means (14, 42) and said separation column (16, 43), said pre-focusing column condensing said specimen that is supplied together with said solvent excluding said protein molecules;

said pre-focusing column (30, 40) having a volume of less than 2.0 ml, said pre-focusing column (30, 40) being packed with a column packing material of a porous support coated by a silicone polymer having a Si—R—X bond (R represents a spacer part, X represents a sulfonic group) and a Si—R' bond (R' represents a hydrophilic group).

2. The liquid chromatograph of claim 1, wherein the hydrophilic group R' is a hydrophilic group containing a hydroxyl group.

3. The liquid chromatograph of claim 1, wherein the spacer part R of said column packing material is formed of a hydrocarbon residue containing 1–40 carbon atoms or a substituent of said hydrocarbon residue in which said carbon atoms are partially substituted by an oxygen atom or a nitrogen atom.

4. The liquid chromatograph of claim 1, wherein said porous support constituting said packing material packed in said pre-focusing column (30, 40) is a silica gel.

5. The liquid chromatograph of claim 1, wherein said separation column has a volume of less than 2.0 ml, and wherein said separation column is a cation-exchange column packed with an ion-exchange packing material having a cation-exchange function.

6. A method of analysis of a specimen containing protein, comprising the steps of:

condensing a specimen containing protein molecules and dispersed in a solvent, to a pre-focusing column, said pre-focusing column condensing said specimen excluding said protein molecules and including a column body having a volume of less than 2.0 ml and packed with a porous support coated by a silicone polymer, said silicone polymer having a Si—R—X bond (R represents a spacer part, X represents a sulfonic group) and a Si—R' bond (R' represents a hydrophilic group) and condensing said specimen dispersed in said solvent;

supplying said condensed specimen to a separation column for separating said specimen dispersed in said solvent; and analyzing said separated specimen by detection means.

7. A method of analysis of a specimen containing protein, comprising the steps of:

supplying a solvent acting as a mobile phase to a flow-path control device by a pump and further supplying a specimen containing protein molecules to said flow-path control device via a specimen injection tube connected to said flow-path control device, said flow-path control device thereby dispersing said specimen in said solvent;

supplying said specimen dispersed in said solvent to a pre-focusing column according to a pumping pressure of said pump exerted on said solvent, said pre-focusing column being packed with a packing material for condensing said specimen;

condensing said specimen by said pre-focusing column excluding said protein molecules;

supplying said condensed specimen to a separation column according to a pumping pressure of said pump exerted on said solvent, said separation column separating said specimen dispersed in said solvent;

supplying said separated specimen to detection means according to a pumping pressure of said pump exerted on said solvent for analyzing said specimen, said pre-focusing column having a volume of less than 2.0 ml, said pre-focusing column being packed by a column packing material of a porous support coated by a silicone polymer, said silicone polymer having a Si—R—X bond (R represents a spacer part, X represents a sulfonic group) and a Si—R' bond (R' is a hydrophilic group).

8. The method of claim 7, wherein said separation column has a volume of less than 2.0 ml and wherein an ion-exchange packing material having a cation-exchange function is packed in said separation column.

9. A method of analyzing a cationic compound in a biological specimen containing protein, by applying a method of analysis of claim 7 or 8 to said biological specimen that contains said cationic compound.

10. A method of analyzing a biological specimen containing a cationic compound and a protein,. by applying a method of analysis of claim 7 or 8 for analyzing said cationic substance in said biological specimen.

11. A method of analyzing a biological tissue specimen containing protein acquired from any of blood plasma, blood serum, saliva and a biological tissue, by applying a method of analysis as claimed in claim 7 or 8 to said biological tissue specimen as said specimen, such that a cationic substance in said specimen is analyzed.

12. A column packing material for selectively condensing a specimen with respect to protein molecules, wherein said material excludes said protein molecule comprising a porous support coated by a silicone polymer, said silicone polymer having a Si—R—X bond (R represents a spacer part, X represents a sulfonic group) and a Si—R' bond (R' represents a hydrophilic group).

13. The column packing material of claim 12, wherein said hydrophilic group R' of said Si—R' bond is a hydrophilic group having a hydroxyl group.

14. The column packing material of claim 12, wherein said spacer part R of said Si—R—X bond is formed of a hydrocarbon residue containing 1–40 carbon atoms or a substituent of said hydrocarbon residue in which said carbon atoms are partially substituted by oxygen atoms or nitrogen atoms.

15. The column packing material of claim 12, wherein said porous support constituting said packing material is a silica gel.

* * * * *